United States Patent [19]

Muto

[11] Patent Number: 4,512,765
[45] Date of Patent: Apr. 23, 1985

[54] SELECTIVE TRACHEAL BRONCHIAL CATHETER

[76] Inventor: Rudolph Muto, 100 Amesbury St., Lawrence, Mass. 01840

[21] Appl. No.: 502,730

[22] Filed: Jun. 9, 1983

[51] Int. Cl.³ .................... A61M 16/00; A61M 25/00
[52] U.S. Cl. ................................................ 604/119
[58] Field of Search ............... 604/119, 118, 280, 281, 604/284, 902, 1, 2, 3, 4; 128/207.14, 207.15, 207.16, 207.17

[56] References Cited

U.S. PATENT DOCUMENTS

| | | | |
|---|---|---|---|
| 1,931,720 | 10/1933 | Edgington | 604/268 X |
| 3,375,828 | 4/1968 | Sheridan | 604/119 |
| 3,399,668 | 9/1968 | Lundgren | 604/280 X |
| 3,608,555 | 9/1971 | Greyson | 604/280 X |
| 3,807,401 | 4/1974 | Riggle et al. | 604/902 X |
| 3,920,023 | 11/1975 | Dye et al. | 604/51 |
| 4,033,331 | 7/1977 | Guss et al. | 604/281 X |
| 4,068,664 | 1/1978 | Sharp et al. | 604/902 X |
| 4,300,550 | 11/1981 | Gandi | 604/119 X |

*Primary Examiner*—William H. Grieb
*Attorney, Agent, or Firm*—Pearson & Pearson

[57] ABSTRACT

A selective tracheal bronchial catheter is provided with a double bend at the distal end and means for twisting the catheter around its longitudinal axis at its proximal end. Thus, the surgeon can selectively cause the tip of the catheter to enter the left main bronchus and upper lobar bronchus without fluoroscopy. Slight withdrawal and 15° twist guides the tip into the left lower lobar bronchus. Slight withdrawal and 180° twist guides the tip into the right main bronchus. Markings on the catheter indicate the degree of twist of the double bend and the distance of insertion. A concentric irrigation tubule, of different material, irrigates and dislodges phlegm, well in advance of the suction tip of the catheter, and self cleans the catheter tip opening.

8 Claims, 12 Drawing Figures

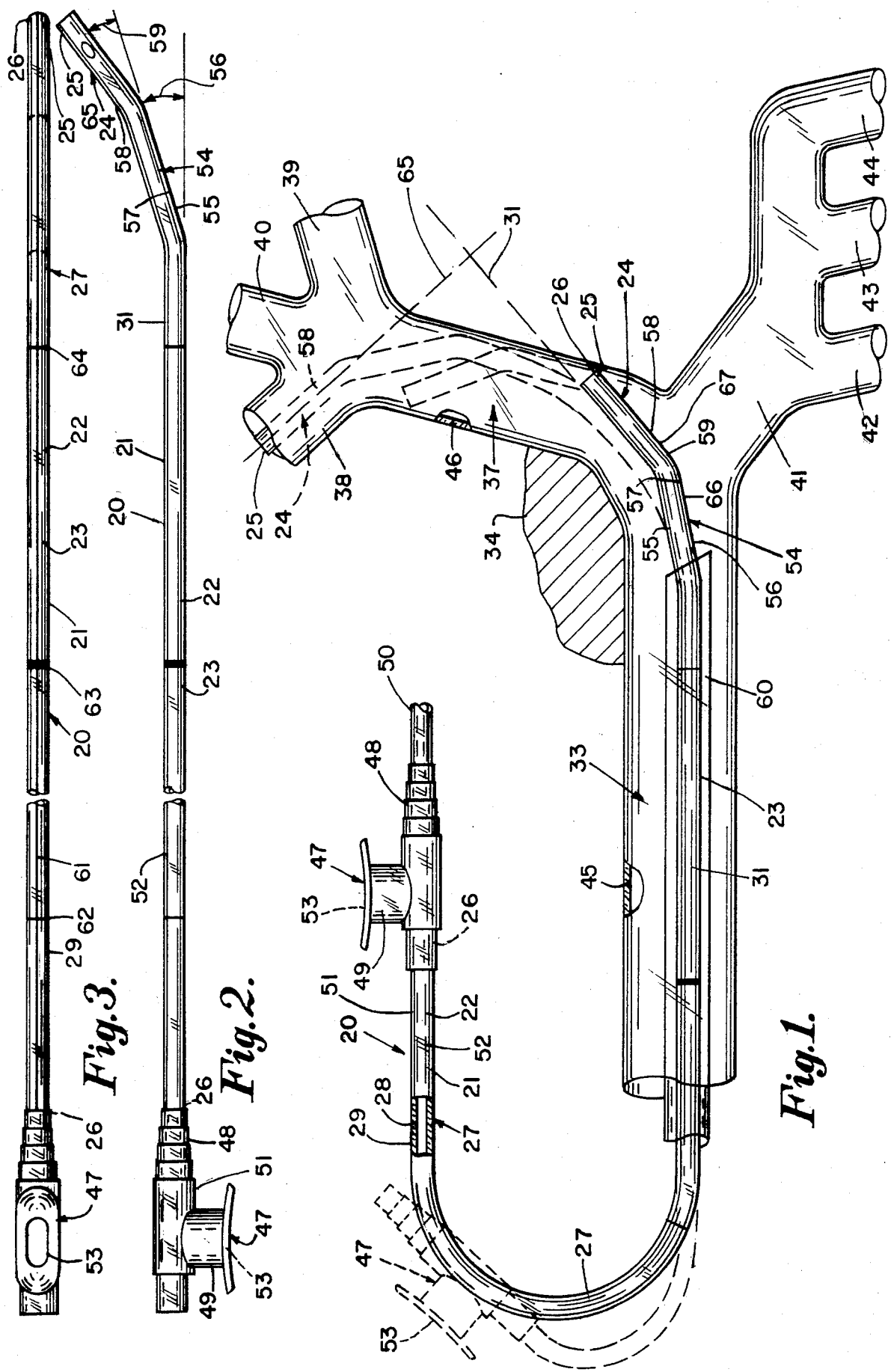

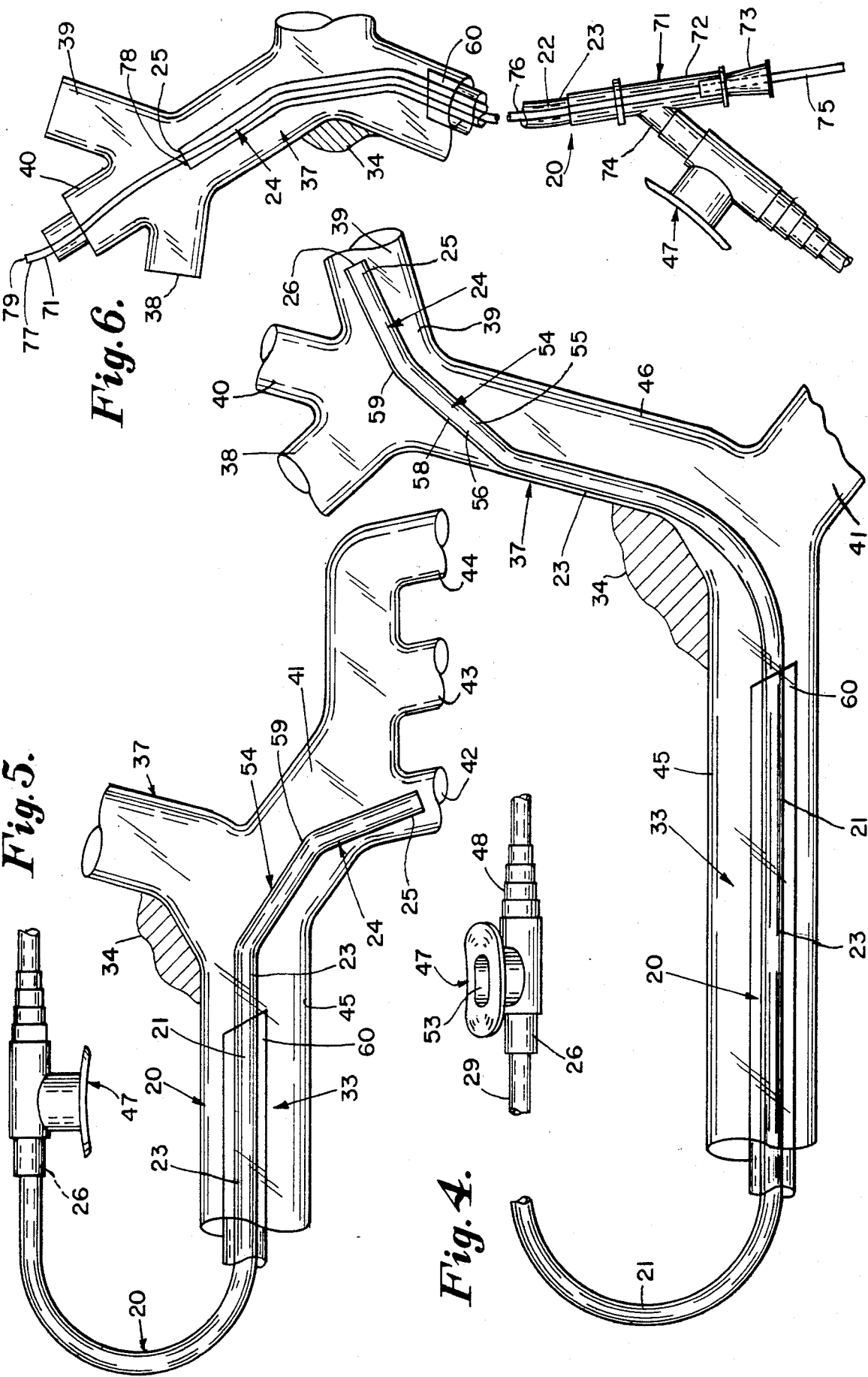

SELECTIVE TRACHEAL BRONCHIAL CATHETER

BACKGROUND OF THE INVENTION

The tracheal bronchial catheters generally in use consist of an elongated tube with a preformed single bend of about 30° away from the normally straight shank of the tube and there is usually a coupling at the proximal end as a suction thumb control device. The difficulty has been that when such a single bend catheter is inserted down the traches the tip at the end of the single bend invariably enters the right main bronchus. Despite twisting around the axis of the catheter it is virtually impossible to cause the bent tip to enter the main left bronchus, unless the patient is being fluoroscoped so that the surgeon can see the tip and gradually induce it to enter the left main bronchus and thence enter the upper and lower lobar bronchus.

Tubular instruments having various types and shapes of bends at the distal end have heretofore been proposed for use in various types of surgery.

For example, U.S. Pat. No. 1,931,720 to Edgington of Oct. 24, 1933 discloses a triple bent tube, apparently of metal, for cleaning the eustachian tubes or pharynx, but two such tubes are required to treat the right and the left.

U.S. Pat. No. 3,807,401 to Riggle, et al of Apr. 30, 1974 also discloses a double bent, hollow tube as a suction device, but the tube is of metal and rigid.

U.S. Pat. No. 3,920,023 to Dye, et al of Nov. 18, 1975 discloses a catheter in the form of a rigid, curved, hollow tube curved for insertion into the bladder.

U.S. Pat. No. 4,068,664 to Sharp, et al of Jan. 17, 1978 discloses a plurality of differently shaped adapter tubes all of which are of rigid material.

SUMMARY OF THE INVENTION

In this invention the single catheter tube is of flexible material and capable of being used to enter the left or the right bronchus by manipulation of the surgeon in twisting the portion extending outside of the body. Thus, no fluoroscope is needed, or if used, the entrance into the left bronchus is made much easier and more rapid.

The suction thumb control, usually used during catheterization is the convenient means used for twisting the double bend catheter of the invention around its longitudinal axis and the double bend projects from the opposite side from the thumb control. The double bend preferably has a first section about 1" to 1¼" long bent away from the shank of the tube at about 30° and has a second section of similar length bent away from the first section at about 30° to terminate in the open ended tip.

A colored line extends along the exterior of the tube to visually indicate, outside the body, the degree of any twist inside the body, and spaced colored rings on the tube exterior tell the surgeon how far the catheter is inserted into the trachea and bronchus.

To enter the left upper lobar bronchus the catheter tip, and the preformed double bent portion of the catheter, uses the inner wall of the left primary, or main bronchus as a guide and/or as a fulcrum so that when the second, or end, section is in the left upper lobar bronchus it is at about 90° to the shank of the tube.

DESCRIPTION OF THE DRAWING

FIG. 1 is a diagrammatic side elevation not necessarily to scale, showing the double bend catheter of the invention in full lines entering the left main bronchus and in dotted lines entering the left upper lobar bronchus;

FIG. 2 is a side elevation of the selective tracheal bronchial catheter of the invention showing the preformed double bend;

FIG. 3 is a top plan view of the catheter shown in FIG. 2;

FIG. 4 is a diagrammatic view similar to FIG. 1 showing the catheter twisted on its axis about 15° to enter the lower left lobar bronchus;

FIG. 5 is a diagrammatic view similar to FIGS. 1 and 4 showing the catheter twisted on its axis about 180° to enter the right main bronchus, and the right upper lobar bronchus;

FIG. 6 is a diagrammatic view similar to FIG. 1 of another embodiment having the tip of an irrigation tubule, in advance of the open tip of the double bend catheter.

DESCRIPTION OF A PREFERRED EMBODIMENT

Figure 7:
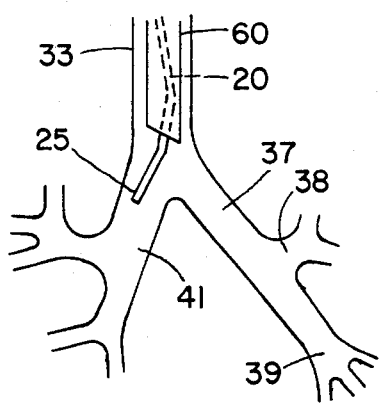
FIGS. 7-12 are diagrammatic views on a reduced scale in sequence, showing the versatility of the double bend catheter of the invention in reaching various locations with slight twist and manipulation by the surgeon.

As shown diagrammatically, and not necessarily to scale, in the drawings the selective, tracheal, bronchial catheter 20, of the invention is preferably formed of transparent, or translucent plastic 21 of predetermined flexibility and is a hollow, cylindrical, elongated tube 22 of uniform diameter. The predetermined flexibility and material of catheter 20, may be the same as that of irrigation catheter No. 467,614, Lot 2KX01 made by Portex, Inc. of Wilmington, Mass. and known in the trade.

The elongated, hollow cylindrical tube 22 includes a normally straight elongated shank 23 having an open distal end 24, terminating in a tip 25, and an open proximal end 26. The shank 23 is intermediate of the ends 24 and 26 and the wall 27 of tube 22 has an interior face 28 and an exterior face 29. The normally straight tube 22 has a central, longitudinal axis 31, but can be bent easily out of its straight configuration to follow the contours of the trachea 33, and other passages in the human body 34 in which similar indwelling devices are inserted by surgeons for the relief, or treatment, of patients.

The portion of the body 34, of a patient, illustrated in FIGS. 1, 4, 5 and 6, includes the trachea 33, left main bronchus 37, left upper lobar bronchus 38 and left lower lobar bronchus 39, and segmental bronchus 40. It also includes the right main bronchus 41, the right upper lobar bronchus 42, the right middle lobar bronchus 43 and the right lower lobar bronchus 44.

The inside face of trachea 33 is designated 45 and the inside face of left main bronchus 37 is designated 46.

A conventional suction thumb control device 47 is provided at the proximal end 26 of tube 22, the straight portion 48 leading to a source of suction not shown and the angular portion 49 extending away from one side 51, of the shank portion 23, the other, or opposite side of the shank portion 23 being designated 52. As is well known, the surgeon applies suction through tube 50, from a suction source, to suction out material from tip 25 through catheter tube 22 only when the aperture 53 in the thumb control device 47 is closed by his thumb. Removal of the thumb opens the tube to atmosphere and causes suction to cease.

Unlike the catheters of the prior art, the catheter 20 is provided with a double bend 54, at the distal end 24, which is preformed to extend away from the other side 52 of the normally straight shank 22 in a direction opposite to the direction of the angular portion 49 of thumb control device 47.

The double bend 54 consists of a first section 55, in the range of one inch to one and one quarter inches in length, and bent angularly away from the longitudinal central axis 31 of normally straight shank 22 at a first angle 56 in the range of about 25° to 35° and preferably at about 30°. The first section has a longitudinal central axis designated 57. It also includes a second section 58 in the range of one inch and one and one quarter inches in length and bent angularly away from the longitudinal central axis 57 of the first section 55, at a second angle 59 in the range of about 25°–35° and preferably at about 30°." Thus, the preformed double bend 54 is proximate the terminal tip 25, and located in the area of the bronchial tubes, when the catheter of the invention is inserted in a tracheal tube in the trachea.

The catheter 20 is provided with a straight line 61, in a contrasting color from the normally transluscent, or transparent, colored plastic 21, line 61 being aligned with the aperture 53 of suction thumb control device 47 and extending all the way down the exterior face 29 to the tip 25 at the open distal end 24. It is also provided with a plurality of measuring rings, in color, such as at 62, 63, and 64 to indicate the quarter, half and three quarter lengths of insertion.

In operation, the selective, tracheal bronchial catheter 20 is inserted down a tracheal tube 60 in the trachea 33 with the thumb control angular portion 49 facing to the right which assures that the tip 25 and double bend 54 will be turned to the left and that the tip 25 will enter main left bronchus 37, as shown in full lines in FIG. 1. The tip 25 and the outer faces 66 and 67 of sections 55 and 58 of double bend 54 slide along the inner faces of the main left bronchus, to guide and fulcrum the tip 25 and double bend 54, as shown in dotted lines. Insertion continues to further increase the angles of bend until the tip 25 enters the left upper lobar bronchus, which is the main objective.

As shown in dotted lines in FIG. 1 when the tip 25 and second section 58 have successfully entered the left upper lobar bronchus, the central longitudinal axis 65 of the second section is then at an angle of about 90° to the portion of the longitudinal central axis 31 of the shank 23 of tube 22, then in the main left bronchus.

As shown in FIG. 4, the catheter 20 may then be withdrawn out of the left upper lobar bronchus and the thumb control device turned through an angle of about 15° which imparts a similar twist to the double bend 54, and tip 25. Advancing the catheter 20 then causes the latter to enter the left lower lobar bronchus as shown.

As illustrated diagrammatically in FIG. 5, the catheter 20 may then be again withdrawn out of the left main bronchus and the thumb control device turned, or twisted, through an angle of 180° which in turn causes the double bend 54 and tip 25 to enter the right main bronchus when advanced, for insertion in the right upper, right middle, and/or right lower lobar bronchi.

The line 61 visually indicates to the surgeon, on the part of the catheter outside the body, whether the part of the catheter, inside the body, is twisted, and how much, while the rings 62, 63, and 64 tell the surgeon how far to insert, or withdraw, the catheter to select the desired bronchus.

As shown in FIG. 6, I prefer to provide a coupling 71 of the Y type, with a suction thumb control device 47 in one Y branch 72 and a slidable plug-like nipple 73 in the other Y branch 74. The nipple 73 is connected by a conduit 75 to a source of irrigation liquid under pressure (not shown) and is connected by a tubule 76 of small diameter, which extends concentrically down tube 22 to a projecting, flexible, elongated tip 77, in advance of tip 25. The irrigation tubule 76 is of a different material than the material of the catheter tube 22, tube 22 preferably being of PVC (polyvinylchloride) and the tubule 76 preferably being of polyethylene so that the tubule will slide easily within the tube.

Thus, by manipulating the nipple 73, the flexible, elongated, small diameter, tip 77 can be rotated, advanced, and retracted relative to the greater diameter open end suction inlet 78, at the distal end 24 of tube 22, to dislodge any phlegm in the lungs. The jetting of irrigation liquid from the small diameter outlet 79 of tubule tip 77 can be taking place several inches in advance of suction being generated in the suction inlet 78, and simultaneously, so that even if the suction tube 22 stops, upon reaching a lung passage of less diameter, the flexible tip 77 can bend, flex and continue on into even smaller diameter passages to clean them out while the relative motion of tubule 76 within the suction inlet 78 serves as a self-cleaning and unplugging element.

A double bend is preferably at the angles of bend specified, because it has been found that three or more bends may cause the catheter to turn back upon itself during insertion. The single bend of the prior art causes the catheter tip to whip around with excessive torque when the catheter is twisted at the proximal end.

The double bend disclosed herein tends to prevent such a whip and to balance torque, so that the double bend catheter tip responds smoothly, without whip, and gently turns on its axis, when within the tracheal tube 60, and when the proximal portion of the catheter is twisted. No torque is thus accumulated to cause the tip 25 to suddenly whip around to an undesired position.

A durometer between 80 and 90 has been found preferable for the material of catheter 20.

Figure 8:
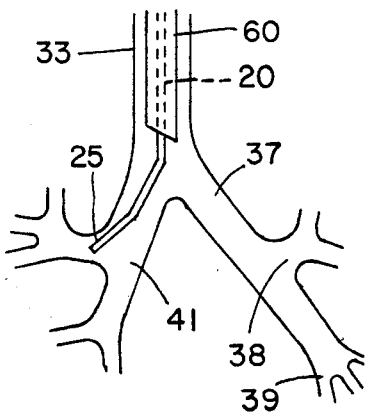
Figure 9:
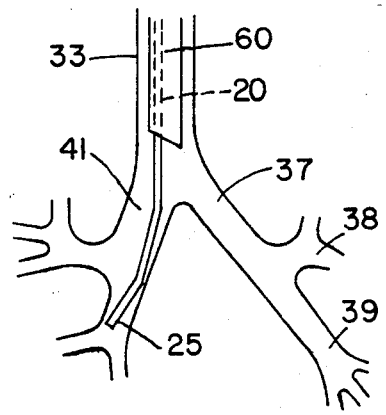
Figure 10:
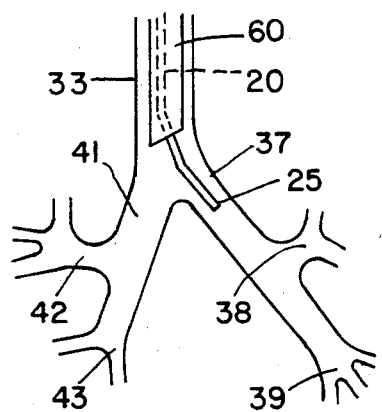
Figure 11:
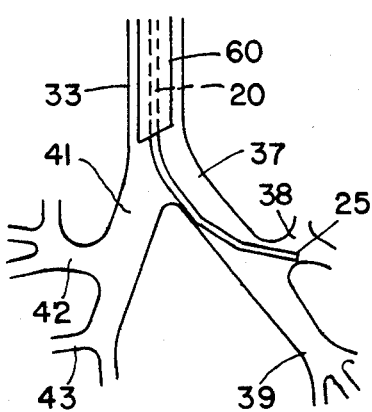
Figure 12:
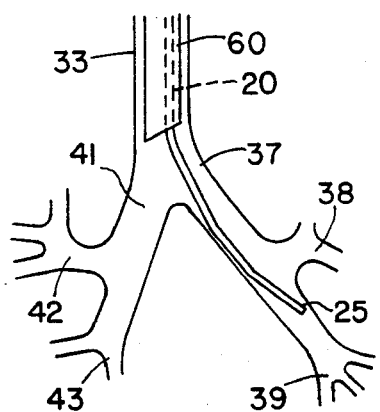

In FIGS. 7 to 12, which are not to scale, there is shown, diagrammatically, a variety of positions which may be selected by the surgeon to cause the double bend catheter of the invention to enter selected bronchi of the patient, with, or without fluoroscopy.

I claim:

1. A selective bronchial catheter comprising: an elongated, hollow cylindrical tube of uniform diameter, and of flexible material, with an open proximal end and an open distal end having a terminal tip;

said tube having a normally straight elongated, intermediate shank portion, with a central longitudinal axis, and a suction thumb control device extending angularly from one side of said shank portion at said proximal end of said tube;

and a preformed, double bend in said tube, extending angularly from the other side of said shank at the distal end of said tube proximate the terminal tip thereof;

said preformed double bend being located in the area of the bronchial tubes and adapted to cause the open distal end of said tube to enter the left main bronchus and then the left upper lobar bronchus, when inserted in a tracheal tube in the trachea.

2. A selective bronchial catheter as specified in claim 1 wherein:
said preformed double bend comprises a first section of said tube bent away from the longitudinal central axis of said shank at an angle in the range of 25°–35°, said section having a central longitudinal axis, and extending for a distance in the range of one inch to one and one quarter inches and a second suction of said tube bent away from the longitudinal central axis of said first section at an angle in the range of 25°–35° and extending for a distance in the range of one inch to one and one quarter inches, said second section terminating in the open distal end of said tube.

3. A selective tracheal bronchial catheter comprising:
an elongated, flexible tube with a normally straight elongated shank with a central longitudinal axis, an open distal end and an open proximal end;
a suction thumb control device extending from one side of said shank near said proximal end;
and a preformed double bend in said tube extending from the other side of said shank near said distal end;
said preformed, double bend terminating in said open distal end and formed by a first section about 1¼ inches in length bent away from said tube at an angle of about 30° and a second section about 1¼ inches in length bent away from said first section at an angle of about 30°;
said double bend being arranged to selectively guide said distal open end into the left upper lobar bronchus of a patient by the use of the inside face of the wall of the main left bronchus as a guide and fulcrum.

4. A selective trachael broncheal catheter as specified in claim 3, wherein:
said elongated flexible tube is of predetermined flexibility such that when said thumb control device is twisted through an angle of about 15°–25° said double bend will twist correspondingly and said open distal end will enter the left lower lobar bronchus.

5. A selective tracheal bronchial catheter, as specified in claim 3 wherein:
said elongated flexible tube is of predetermined flexibility such that when said thumb control device is twisted through an angle of about 180° said double bend will twist correspondingly and said open distal end will enter the right main bronchus.

6. A selective tracheal bronchial catheter comprising:
an elongated, hollow cylindrical tube of uniform diameter, and of predetermined flexibility, said tube having a central longitudinal axis, an open distal end and an open proximal end;
said tube having a normally straight elongated shank with a preformed double bend at the distal end terminating in said open distal end, said double bend including a first section bent away from said shank at about 30° and a second section bent away from said first section at about 30°;
and means, near the proximal end of said tube, for twisting the tube around its longitudinal axis to cause the open distal end of said double bend to selectively enter the left main bronchus, left upper lobar bronchus, left lower lobar bronchus or the right main bronchus.

7. A selective tracheal bronchial catheter as specified in claim 6 wherein:
an elongated irrigation tubule, of substantially less outside diameter than the inside diameter of said catheter tube, is slidably and rotatably sleeved within said catheter tube, said tubule having means at its proximal end for manipulating its distal end; said distal end being flexible and adapted to project beyond the open distal end of said catheter tube for dislodging phlegm in narrow passages, and said catheter and tubule being of different materials.

8. A selective tracheal bronchial catheter as specified in claim 7 wherein:
said catheter tube is of polyvinylchloride and said irrigation tubule is of polyethylene.

* * * * *